United States Patent [19]

Jhingan

[11] Patent Number: 5,350,686
[45] Date of Patent: Sep. 27, 1994

[54] MICROWAVE ACCELERATION OF ENZYME-CATALYZED MODIFICATION OF MACROMOLECULES

[75] Inventor: Anil K. Jhingan, Polk County, Iowa

[73] Assignee: Pioneer Hi-Bred International, Inc., DesMoines, Iowa

[21] Appl. No.: 869,604

[22] Filed: Apr. 16, 1992

[51] Int. Cl.$^5$ .......................... C12N 13/00; A61L 2/00
[52] U.S. Cl. .............................. 435/173.2; 435/173.1; 422/21
[58] Field of Search .................. 435/173, 173.1, 173.2; 422/21

[56] References Cited

U.S. PATENT DOCUMENTS

| | | | |
|---|---|---|---|
| 3,432,413 | 3/1969 | Vanderhoff | 524/832 |
| 3,663,394 | 5/1972 | Kawahara | 204/168 |
| 3,926,556 | 12/1975 | Boucher | 422/21 |
| 4,117,220 | 9/1978 | Worman | 528/503 |
| 4,800,899 | 1/1989 | Elliott | 607/156 |
| 5,060,414 | 10/1991 | Wayland | 47/1.3 |

OTHER PUBLICATIONS

Jhingan (1992) *Meth. Molec.. Cell Biol.*, 3, 15–22.
Narasimhan et al. (1991) *Biochem. Int.*, 25(2), 363–70, in *Chem. Abst.*, 116(7), 405, Abst No. 54644.
Garibov et al. (1990) *United States Patent Sovrem. Biol.*, 110(2), 306–20, in *Chem. Abst.*, 115(7), 388, Abst. No. 67530.
Byus et al. (1988) *Cancer Res.*, 48(15), 4222–4226.
V. Ya. Maleev, et al., entitled "Does DNA Absorb Microwave Energy" Biopolymers, vol. 26, (1987) pp. 1965–1970.
E. I. Obukhan entitled "Mitotic Activity of Myelocaryocytes under Microwave Radiation (2375 MHz)" UDK 613.64:576.35.
V. Ya. Maleev, et al., entitled "Absorption of DNA Solutions in the 9–12 GHz Frequency Range" Biopolymers and Cell, 1986, vol. 2, No. 1, pp. 35–38 (UDK 577.32).

*Primary Examiner*—Douglas W. Robinson
*Assistant Examiner*—Jon P. Weber
*Attorney, Agent, or Firm*—Nina L. Pearlmutter; Michael J. Roth

[57] ABSTRACT

A method of enhancing the enzyme-catalyzed modification of macromolecules comprising exposure of the enzyme and its macromolecule substrate to microwaves is disclosed. A frequency of from 1800 to 3000 MHz and a power of from 50 to 100 watts is preferred. The procedure is rapid, efficient, and suitable for many enzyme-catalyzed reactions. The method can be used for restriction endonuclease digestion of DNA samples and facilitates one of the time-consuming procedures of nucleic acid research. The method is also adaptable for automated procedures in biological research.

15 Claims, No Drawings

MICROWAVE ACCELERATION OF ENZYME-CATALYZED MODIFICATION OF MACROMOLECULES

TECHNICAL FIELD

A novel technique using microwave energy for enzymatic digestion of DNA molecules is disclosed.

BACKGROUND OF THE INVENTION

The enzymatic digestion of isolated DNA from procaryotes, eucaryotes, and plasmids is a time-consuming but necessary step for further gene studies and requires consistent cleavage of DNA molecules or segments at specific sites. Several factors can affect the outcome. Variations in yield and quality of the cleaved fragments from digestion to digestion probably result from inconsistent temperatures and enzymatic activity that occur over the hours it may take to effect complete digestion of large macromolecules. Impurities in DNA samples may retard processing and produce inconsistent products.

Traditionally, digestions of DNA with restriction endonucleases are carried out in a buffer containing salts and reducing agent in an incubator at 37° C., considered to be the optimum temperature for activity of most enzymes. Sambrook, J., Fritsch, E. F., and Maniatis, T., *Molecular Cloning: A Laboratory Manual*, 2nd ed., Cold Spring Harbor Laboratory, Cold Spring Harbor, New York (1989). The incubation time varies with the type and quality of DNA and the particular restriction endonuclease used. Although the digestion of plasmid DNA with some enzymes can be achieved in 1 hour using a large amount of enzyme, in general, cleaving genomic DNA with restriction endonucleases takes from eight hours to overnight and thus is a time-consuming technique by conventional methods. Accordingly, there remains a need for a rapid, efficient, and consistent procedure for digesting DNA.

The effects of microwave energy on chemical processes has been studied for many years. Abramovitch, et al., *Org. Prep. Proced. Int.* (1991) 23:683–711. Microwaves have been used to drive the synthesis of radiopharmaceuticals (Hwang, et al., *J. Chem. Soc., Chem. Commun.* (1987) 23:1799–801), hydrolyses (Abramovitch, et al., (1991) *Tetrahedron Let.* 32:5251–54), polymerizations (U.S. Pat. No. 3,432,413), and the synthesis of organic compounds (Gedye, et al., *Can. J. Chem.* (1991) 69:706–11; Ito, et al. *J. Mol. Evol.* (1990) 31:187–94). Hydrolysis of biological materials has also been studied. Jahngen, et al., *J. Org. Chem.* (1990) 55:3406–9; Margolis, et al., *J. Auto. Chem.* (1991) 13:93–95; Feinberg, et al. (1991) *Analusis* 19:47–55.

However, when living systems or tissues are exposed to concentrated microwave energy, the effects have been deleterious for the most part. Belkhode, et al., *J. Microwave Power* (1974) 9:23–29; Galli, et al., *Meth. Enzymology* (1982) 86:635–642; Huai, et al., *J. Bioelectricity* (1984) 3:361–366; Baranski S., *Amer. J. Phys. Medicine* (1972) 51:182–191. Microwave radiation inhibits the synthesis of DNA and increases chromosome aberrations. Garaj-Vrhovac, V., et al., *Mutation Res.* (1990) 243:87–93. Blocked DNA synthesis in irradiated cells and increased reproduction in uninjured cells was suggested to explain an initial decrease followed by an increase in mitotic activity of myelocaryocytes after irradiation with microwaves. Obukhan, E. I., *Tsitol. Genet.* (1984) 18:264–267 (translation provided).

In some studies however, the results of irradiation exposure have been less clearcut. An increase in cellular synthesis or enzyme activity has been noted. Byus, et al., *Cancer Res.* (1988) 48:4222–4226. Several investigators have found irradiation with microwaves has no effect on enzyme activity or DNA repair synthesis. Ward, et al., *J. Microwave Power* (1975) 10:315–320; Meltz, et al., *Radiat. Res.* (1987) 110:255–66. Other reports show both enhancement and repression of cellular enzyme activity. Dutta, S. K. and Verma, M., Curr. Sci. (1989) 58:58–63; Dutta, S. K. and Verma, M., *Curr. Sci.* (1988) 57:779–786.

Whether inducing or inhibitory, most of the observed microwave effects have been attributed to the increased temperature due to energy exposure, Belkhode, et al., *J. Microwave Power* (1974) 9:23–29, although the results of some studies indicate that thermal effects alone are not responsible for all of the consequences observed. Baranski, supra.

The syntheses, hydrolyses, and other modifications of large molecules done with microwave irradiation have utilized only simple inorganic or organic reagents such as sulfuric acid or sodium hydroxide. Furthermore, when microwave energy has been applied to drive limited, single-step chemical reactions, the results have been variable. Inconsistent temperatures, other reagents, and the absorption properties of the molecules themselves may be responsible for much of this variability. Gedye, supra; Belkhode, supra.

Although there have been reports that DNA molecules absorb microwave energy, other studies show that ions and water molecules can account for such absorption. Davis, et al., *Biopolymers* (1989) 28:1429–1433; Gabriel, et al., *Biophys. J.* (1989) 55:29–34; Maleev, et al., *Biopolymers* (1987) 26:1965–1970; Maleev, et al., *Biopolim Kletka* (1986) 2:35–38 (translation provided). As described above, investigations of DNA synthesis or repair following irradiation with microwaves have measured an increase in inhibition or damage, suggesting that DNA and the enzymes that are involved in synthesis, division, and repair are deleteriously affected by exposure to microwaves.

Recent observations of isolated DNA molecules treated with microwave energy have supported these hypotheses. Following exposure to microwave energy, plasmid DNA exhibited single-strand breaks, localized strand separations, and pseudo-restriction sites. Narasimhan, V. and Huh, W. K., *Biochem. International* (1991) 25:363–370. The number of single- and double-strand breaks increases in a linear relationship to both the power applied and the duration of exposure to microwaves. Sagripanti, et al., *Radiat. Res.* (1987) 110:219–231. No investigators have endeavored to drive enzyme-catalyzed reactions on biological molecules using microwave energy, especially large macromolecules such as DNA or RNA. In fact, microwaves appear to be avoided as an energy source for this step in macromolecule research. For example, Stroop, et al., *Anal. Biochem.* (1989) 182: 222–225, found that DNA could be denatured in a process using microwave energy without apparent damage, but nevertheless chose to enzymatically digest the DNA by standard procedures prior to microwave denaturation.

Disclosure of the Invention

It has now been discovered that exposing a digestion mixture containing nucleic acid molecules and an enzyme which cuts such molecules to microwave radiation can complete the enzymatic digestion process cleanly and accurately, and in a considerably shorter time than conventional methods. While common experience with microwave cooking might lead one to expect an improvement in speed of digestion, the discovery that the reaction is clean and accurate is contrary to published reports of strand breaks and other damage to DNA as a result of irradiation. Sagripanti, supra; Narasimhan, supra.

Although the specific embodiment illustrated herein focuses on the delicate and complex cleavage of DNA with restriction endonucleases, it has now been determined that the method of this invention can be employed to accelerate any enzyme-catalyzed reaction with little manipulation of irradiation time and energy level. All of the enzymes tested were fully active when used within their working exposure period. The reactions are complete in few minutes, the results are highly reproducible, and the process is amenable to automation. Accordingly, this invention provides a method for enzymatic modification of a biological macromolecule, comprising the step of irradiating a composition comprising the biological macromolecule and an enzyme with sufficient microwave energy to accelerate the activity of the enzyme. The biological macromolecules useful in this invention include DNA and RNA strands, proteins, polysaccharides, mucopolysaccharides, and similar polymeric enzyme substrates. The enzyme can be one or more of the many restriction endonucleases in the case of DNA or RNA, or a protease, saccharidase, or other enzyme for which the macromolecule is a substrate.

While not intending to be limited by theory, it appears that the DNA helix absorbs enough microwave energy to rotate portions of the molecule, or through localized superheating parts of the helix open out or are denatured, so that proper orientation for enzymatic strand scission is provided. However, at present it is difficult to speculate on an exact mechanism of catalysis.

As a result, this use of microwave irradiation provides a remarkable decrease in the time necessary to carry out complete and reproducible digestions of DNA using only 8–11 units of most enzymes. The procedure is promising especially for the digestion of genomic DNA which is routinely used by many researchers and can facilitate ligation, cloning, and vector construction experiments. The rapidity and cost savings of this method makes it a potentially new general method to digest DNA and to provide a basis for automating digestion as well as other types of molecular modifications requiring the use of enzymes. Accordingly, in a preferred embodiment this invention provides a method for enzymatic digestion of nucleic acids comprising the step of irradiating a composition comprising a nucleic acid and an enzyme with sufficient microwave energy to accelerate the activity of the enzyme.

Microwave energy comprises wavelengths of about 0.3 to 30 cm, corresponding to frequencies of 1–100 gigahertz, and is found between the radio and the infrared regions of the electromagnetic spectrum. The amount of electromagnetic energy absorbed by a living organism is determined by the dielectric properties of the tissues, cells, and biological molecules.

The generation of the microwave energy is not critical and can be by any means known to the art. In fact, a highly preferred means of applying microwave radiation to unautomated reactions is the microwave oven that is part of the standard equipment in most biological laboratories. Such microwave ovens have maximum power levels of from 500 watts to about 1000 watts. Even the smallest ovens provide ample levels of microwave irradiation for use in this invention and accordingly, it will be convenient to use lower power settings on ovens in which the output power is adjustable.

In a preferred embodiment of this invention, lower power settings are also used to time-distribute the applied power over a longer time interval and minimize the potential for localized energy uptake and resulting molecular damage. In an especially preferred embodiment, microwave power is applied to the sample over a series of intervals, with "rest" intervals, in which microwave power is not applied to the sample. Power application intervals and rest intervals will conveniently range from 1 to 60 seconds each, with power application intervals of from 15 to 60 seconds and rest intervals of from 0.5 to 5 seconds being preferred. Most preferably, power will be applied for intervals of about 45 seconds, separated by rest intervals of 1 to 2 seconds. Other intervals were tested but 45 seconds produced more consistent results than shorter or longer periods. The intervening rest intervals prevent adverse thermal effects and can be as brief as 1–2 seconds.

It is to be understood that in a preferred mode of practicing this invention, these efforts to distribute the applied power over time are to be taken in addition to using "power" settings of the apparatus below maximum. In fact, many commercial microwave ovens maintain a constant magnetron output power at 650–900 watts and modulate applied power by varying the duty cycle of the magnetron, a setting of "1" corresponding to a 10% duty cycle and a setting of "9" corresponding to a 90% duty cycle. Most preferably, settings of from 1 to 8, i.e. a magnetron duty cycle of from 10% to 80% at an output power of 700 to 800 watts, will be used. That aggregate output energy, corresponding to from about 70 watt-seconds to 35,000 watt-seconds, preferably from 3000 to 3500 watt-seconds per interval, will be applied in the intervals described above.

The number of irradiation intervals employed in the Examples ranged from 1 to 42. The optimum number required for digestion of the isolated DNA with various restriction endonucleases was determined by irradiating the samples over a range of intervals coupled with an analysis of the resulting DNA products for uniform and complete cleavage following electrophoresis and ethidium bromide staining on agarose gels. The preferred range of total exposure time for most enzymes was between 6 to 15 minutes (8–20 intervals) at power level one. Within this range, the microwave energy exposure was sufficient to accelerate the enzyme activity to a level that resulted in complete digestion of the nucleic acid sample.

Increasing the amount of radiation by using a higher power setting as described above, in most cases, will decrease the total exposure time. However, there is considerable variation in wattage produced among microwave ovens due to differences in the individual power supply output provided to the magnetrons of the respective ovens. As a result, magnetron output powers may vary from 600–1000 watts. Using a lower power setting increases the total time range over which the individual enzymes will work and reduces the possibility that the power output is too low or too high for the optimal activity of an enzyme in a particular oven. Furthermore, an increased range of exposure times allows the simultaneous use of many different enzymes working at a 100% activity level without enzyme degradation. At the most preferred exposure level, power setting one, the majority of enzymes tested exhibited 100% activity within the same total exposure periods.

Also determined was the maximum number of intervals beyond which enzyme activity was inhibited and the resulting digestion was incomplete. It is likely that this inhibition is due to degradation of the enzyme structure rather than or, in addition to, damage to the DNA molecule, because complete cessation of enzyme activity occurred at different times using the same type of DNA and different enzymes. Under these conditions, no low molecular weight bands were observed on the agarose gels, with the exception of one band in one sample at a very high power setting. Instead, an increase in the amount of undigested DNA or high molecular weight DNA is observed.

In the following non-limiting examples, the amounts of enzyme required for microwave digestion were comparable to those used in conventional digestions. The amount of DNA tested was also the same except that 5 $\mu$g of plasmid DNA was used in all samples instead of 1 $\mu$g or less.

The data accumulated for different times and power settings indicates that there is a reasonable range over which restriction endonucleases are active for complete and consistent digestion. Thus it is clear that numerous specific embodiments of the methods of this invention can be optimized to suit the specific reaction system under consideration. Furthermore, the facility of this invention shows the applicability of this technique to other microwave equipment with different settings and power output.

EXAMPLE 1

Irradiations were conducted using an Amana brand microwave oven (Model R 311 T, 700 W). Genomic DNA was isolated from several plant species using standard methods well-known and commonly applied in the art, as well as the method of Jhingan, A., *Meth. Mol. Cell. Biol.* (1992) 3:15–22. Samples of several different types of plasmid DNA were also used. Five $\mu$g of each genomic DNA sample in a 30 $\mu$l reaction volume or 5 $\mu$g of plasmid DNA in 20 $\mu$l reaction volume containing buffer and 8-11 units of the appropriate restriction enzyme (Boehringer Mannhein) in 1 $\mu$l (except HindIII) was irradiated for 45 second (45s) time intervals in a 0.5 ml Eppendorf tube. The digestions using HindIII required twice as much enzyme (20 units). The reaction was terminated by the addition of 0.5M EDTA (pH 8) to a final concentration of 10 mM and the addition of gel-loading dye.

Identical samples, treated at 37° C. for the same total period of time as required for microwave digestion and for longer times (1 h, plasmid DNA; 6 h, genomic DNA) served as controls. In addition, to determine if the DNA samples would degrade or break as a result of irradiation alone, samples of the digestion mixtures were prepared without enzyme and subjected to the same exposure periods in the microwave oven as the enzyme-containing samples. The DNA in these samples remained undigested following treatment and no degradation products were observed.

The results of microwave exposure and minimum number of periods for complete digestion of maize genomic DNA and several plasmid DNAs with various restriction endonucleases are shown in Table I. The number of irradiation periods required to digest the various DNA samples with individual enzymes fell within a fairly narrow range. Separately, restriction fragment analysis was performed on the various samples, and genomic DNA digestion patterns were analyzed by means of Southern blots. It was found that the restriction pattern of the microwave-irradiated samples following electrophoresis was identical with samples that were digested at 37° C. for longer periods of time under conventional conditions. Most control samples incubated at 37° C. for the same time periods only exhibited partial digestion products; a few samples of plasmid DNA were nearly completely digested.

Variable EcoRI digestion of some plasmid DNAs suggested that impurities which inhibited the activity of EcoRI were present in some of the plasmid preparations. This is consistent with prior art that reports impure DNA samples require more enzyme and longer incubation times for complete digestion of DNA. However, digestion of genomic DNA using EcoRI gave highly reproducible results, indicating that the source of the variability was the samples used and not the method.

From these results it was concluded that microwave irradiation enables a more rapid and efficient digestion of DNA than conventional heating. In fact, the digestion rate using microwave energy was as much as 1100 times as fast as that of the conventional heating procedure, indicating the utility of this technique in terms of remarkable time savings and producing results contrary to that of published reports regarding the inactivation of enzymes by exposure to microwaves.

EXAMPLE 2

To determine if combinations of enzymes would effectively cleave the DNA samples, EcoRI and PstI were combined with plasmid DNA and subjected to microwave energy. The plasmid DNA was completely digested following 8 exposure intervals at power level one. The entire process took approximately the same amount of time as required for either enzyme used alone and the results were consistent with those obtained by conventional methods.

EXAMPLE 4

One endpoint of the digestion process was investigated further by increasing the number of exposure intervals above optimum in order to find out when the activity of the endonucleases were inhibited. The results for cleavage of genomic DNA are shown in Table II. All enzymes required at least twice the threshold exposure before diminished activity was observed with the exception of HindIII which appears to have a narrower range of optimal activity.

EXAMPLE 5

Another endpoint of the digestion process was also investigated by increasing power levels in order to find out when the activity of the endonucleases were inhibited. The results for digestion of various plasmid DNAs are shown in Table III.

Depending on the plasmid DNA species, inhibition or deactivation occurred over a range of exposure intervals. For one enzyme (BamHI), exposure time rather than increased energy level resulted in inhibition. All other enzymes, however, were inhibited in shorter time periods as the power level increased.

TABLE I

Threshold for Complete Digestion by Microwave Energy at Power Level One

Maize Genomic DNA

| Enzyme | # of 45s intervals | Total (min) |
| --- | --- | --- |
| BamHI | 2 | 1:30 |
| BglII | 12 | 9 |
| EcoRI | 9 | 6:45 |
| EcoRV | 9 | 6:45 |
| HindIII | 30 | 22:30 |
| KpnI | 9 | 6:45 |
| SstI | 12 | 9 |

Plasmid DNA

| Enzyme | Plasmid | # of 45s intervals | Total (min) |
| --- | --- | --- | --- |
| PvuII | pGEM-3Z f(+)− | 20 | 15 |
| PvuII | pUC 18 | 32 | 24 |
| EcoRI | pUC 18 | 8 | 6 |
| BamHI | other | 6, 8 | 4:30, 6 |
| BglII | " | 12 | 9 |
| EcoRV | " | 8 | 6 |
| HindIII | " | 12 | 9 |
| PstI | " | 6, 8, 22 | 4:30, 6, 16:30 |
| PvuII | " | 26, 28 | 19:30, 21 |
| NcoI | " | 14 | 10:30 |
| HpaI | " | 26 | 19:30 |

TABLE II

Threshold for Enzyme Inactivation by Microwave Energy

Maize Genomic DNA

| Enzyme | # of 45s intervals | Power level | Total (min) |
| --- | --- | --- | --- |
| BamHI | 20 | 8 | 15 |
| BglII | 30 | 1 | 22:30 |
| EcoRI | 20 | 1 | 15 |
| EcoRV | 20 | 1 | 15 |
| HindIII | 38 | 1 | 28:30 |
| KpnI | 20 | 5 | 15 |
| SstI | 30 | 1 | 22:30 |

TABLE III

Threshold for Enzyme Inactivation by Microwave Energy at Different Power Levels[1]

Plasmid DNAs

| Enzyme | Power Level | # of 45s intervals | Total (min) |
| --- | --- | --- | --- |
| BamHI | 4 | 20 | 15 |
| BamHI | 5 | 20, 22 | 15, 16:30 |
| BamHI | 6 | 20 | 15 |
| BglII | 5 | 30 | 22:30 |
| EcoRI | 1 | 14 | 10:30 |
| EcoRV | 5 | 20 | 15 |
| NcoI | 1 | 18 | 13:30 |
| HpaI | 3 | 42 | 31:50 |
| PvuII | 1 | 32, 40 | 24, 30 |
| PvuII | 2 | 20, 28 | 15, 21 |
| PstI | 2 | 30 | 22:30 |
| PstI | 4 | 26 | 19:30 |
| PstI | 5 | 20 | 15 |

[1]Power levels in this example correspond to 1/10 of the % duty cycle of the magnetron, e.g., at level 2 the magnetron is radiating 20% of the time. Some microwave ovens control power output of the magnetron by using switching power supplies which transmit varying numbers of AC cycles to the rectifier bridge, with or without a time shift, thereby controlling the power output of the DC power supply to the anode of the magnetron. While this invention does not relate to the specific microwave apparatus employed per se, the use of such an apparatus to provide microwave irradiation is entirely contemplated and provides equivalent results in the practice of this invention.

What is claimed is:

1. A method for enzymatic modification of a biological macromolecule comprising the step of exposing a composition comprising the biological macromolecule and an enzyme for which the macromolecule is a substrate to microwaves at a frequency of from 1800 to 3000 MHz and a power of from 50 watts to 1000 watts to accelerate the activity of the enzyme.

2. A method according to claim 1 wherein the biological macromolecule is DNA or RNA.

3. A method according to claim 2 wherein the biological macromolecule is DNA and the enzyme is a DNA restriction endonuclease or a mixture thereof.

4. A method according to claim 1 wherein the total irradiation time is from 1 to 35 minutes.

5. A method according to claim 4 wherein the composition is irradiated for intervals of from 1 to 60 seconds.

6. A method according to claim 4 wherein the composition is intermittently irradiated by exposure to microwave radiation for intervals of from 1 to 60 seconds, the intervals of exposure to microwave radiation being separated by intervals of non-exposure to microwave radiation of from 1 to 60 seconds.

7. A method according to claim 6 wherein the irradiation intervals are about 45 seconds and the non-irradiation intervals are from 1 to 2 seconds.

8. A method according to claim 5 wherein the microwave radiation is supplied by a magnetron having a duty cycle during the irradiation intervals of from 10% to 80%.

9. A method according to claim 8 wherein the magnetron has an output power of from 650 to 900 watts.

10. A method according to claim 3, wherein the total irradiation time is from 1 to 35 minutes.

11. A method according to claim 10, wherein the said composition is irradiated for intervals of from 1 to 60 seconds.

12. A method according to claim 10, wherein the composition is intermittently irradiated by exposure to microwave radiation for intervals of from 1 to 60 seconds, the intervals of exposure to microwave radiation being separated by intervals of non-exposure to microwave radiation of from 1 to 60 seconds.

13. A method according to claim 12 wherein the irradiation intervals are about 45 seconds and the non-irradiation intervals are from 1 to 2 seconds.

14. A method according to claim 11 wherein the microwave radiation is supplied by a magnetron having a duty cycle during the irradiation intervals of from 10% to 80%.

15. A method according to claim 14 wherein the magnetron has an output power of from 650 to 900 watts.

* * * * *